United States Patent
Flohr et al.

(10) Patent No.: US 8,744,161 B2
(45) Date of Patent: Jun. 3, 2014

(54) METHOD AND COMPUTER SYSTEM FOR SCATTERED BEAM CORRECTION IN A MULTI-SOURCE CT

(75) Inventors: Thomas Flohr, Uehlfeld (DE); Martin Petersilka, Adelsdorf (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 144 days.

(21) Appl. No.: 13/401,879

(22) Filed: Feb. 22, 2012

(65) Prior Publication Data
US 2012/0213424 A1    Aug. 23, 2012

(30) Foreign Application Priority Data
Feb. 23, 2011 (DE) .......................... 10 2011 004 598

(51) Int. Cl.
*G06K 9/00* (2006.01)

(52) U.S. Cl.
USPC .......................................... 382/131

(58) Field of Classification Search
USPC ............. 382/128, 131; 250/333, 363.04, 582, 250/584; 378/4, 7, 11, 21, 25
See application file for complete search history.

(56) References Cited

U.S. PATENT DOCUMENTS

| | | | |
|---|---|---|---|
| 6,421,412 B1 * | 7/2002 | Hsieh et al. ........................ | 378/9 |
| 6,639,964 B2 * | 10/2003 | Schneider et al. ................ | 378/7 |
| 7,039,153 B2 * | 5/2006 | Bruder et al. ..................... | 378/9 |
| 7,542,540 B2 * | 6/2009 | Matsuda ............................ | 378/7 |
| 7,680,241 B2 | 3/2010 | David et al. | |
| 7,782,996 B2 | 8/2010 | Rührnschopf et al. | |
| 7,835,485 B2 | 11/2010 | Bruder et al. | |
| 7,957,502 B2 * | 6/2011 | Manabe et al. .................... | 378/7 |
| 2003/0128801 A1 * | 7/2003 | Eisenberg et al. ............... | 378/19 |
| 2004/0034269 A1 * | 2/2004 | Ozaki ............................... | 600/1 |
| 2004/0114710 A1 * | 6/2004 | Ozaki ............................... | 378/9 |
| 2004/0213371 A1 * | 10/2004 | Bruder et al. ..................... | 378/9 |
| 2006/0083351 A1 * | 4/2006 | Lamberty et al. ............... | 378/86 |

(Continued)

FOREIGN PATENT DOCUMENTS

| | | |
|---|---|---|
| DE | 102005048397 A1 | 4/2007 |
| DE | 102006046047 A1 | 4/2008 |
| DE | 102007014829 B3 | 9/2008 |

OTHER PUBLICATIONS

Kalender WA. Calculation of x-ray grid characteristics by Monte Carlo methods Phys Med Biol, 1982, 27(3): pp. 353-361; Magazine.

(Continued)

*Primary Examiner* — Daniel Mariam
*Assistant Examiner* — Shervin Nakhjavan
(74) *Attorney, Agent, or Firm* — Harness, Dickey & Pierce, P.L.C.

(57) ABSTRACT

A method and a computer system are disclosed for scattered beam correction in a CT examination of an object in a multi source CT. In at least one embodiment, the method includes generating original projection data records; reconstruction of the object with the original projection data records of at least one detector; determining the scattered radiation generated by each emitter exclusively in the direction of the original beams of the at least one other emitter relative to its opposing detector; generating corrected projection data records by removing the calculated scattered radiation from the original projection data records; reconstruction of the object with the corrected projection data records, and implementing a further iteration of the method when determining the scattered radiation or issuing the reconstruction result if at least one predetermined abort criterion applies.

26 Claims, 4 Drawing Sheets

(56) References Cited

U.S. PATENT DOCUMENTS

| | | |
|---|---|---|
| 2007/0086561 A1 | 4/2007 | Bruder et al. |
| 2007/0253524 A1* | 11/2007 | Bruder et al. ............... 378/7 |
| 2007/0253525 A1* | 11/2007 | Popescu ...................... 378/7 |
| 2008/0159469 A1* | 7/2008 | Ruhrnschopf et al. ...... 378/4 |
| 2008/0292170 A1* | 11/2008 | Bruder et al. ............. 382/131 |
| 2010/0189376 A1* | 7/2010 | Bertram et al. ........... 382/274 |
| 2010/0208870 A1* | 8/2010 | Zou et al. .................. 378/87 |

OTHER PUBLICATIONS

Nicolas Freud et al. A Hybrid Approach to Simulate X-Ray Imaging Techniques, Combining Monte Carlo and Deterministic Algorithms IEEE Transactions on Nuclear Science, vol. 52, No. 5, Oct. 2005 pp. 1329-1334; Magazine; 2005.

German Search Report for German Application No. 10 2011 004 598.8 (Not Yet Published).

German Priority document for German Application No. 10 2011 004 598.8 (Not Yet Published).

* cited by examiner

METHOD AND COMPUTER SYSTEM FOR SCATTERED BEAM CORRECTION IN A MULTI-SOURCE CT

PRIORITY STATEMENT

The present application hereby claims priority under 35 U.S.C. §119 to German patent application number DE 10 2011 004 598.8 filed Feb. 23, 2011, the entire contents of which are hereby incorporated herein by reference.

FIELD

At least one embodiment of the invention generally relates to a method and/or a computer system for scattered beam correction in a CT examination of an object in a multi-source CT, whereby the scattered beam correction is iteratively run on the projection data.

BACKGROUND

In the dual-source CT, by way of the simultaneous use of two emitter detector systems, x-ray quanta on the object to be measured are scattered by an x-ray emitter of a first emitter detector system into a detector of a second emitter detector system which is arranged angularly offset on the same gantry and vice versa. In order to prevent artifacts, this so-called transverse scattering must be corrected with suitable methods. To this end, the knowledge of the profile of the scattered beam intensity is needed in each projection.

To this end, the following 3 methods are essentially known:
(i) the model-based estimation of the scattered radiation from sinogram data, based on data which chronologically predates the point in time of the correction.
(ii) the measurement of the scattered radiation with the aid of dedicated sensors.
(iii) the alternate blanking of the respective primary radiation and direct measurements of the transverse scattering during the blanking phase.

It is common to all three variants that the scattered beam correction of the raw data is implemented once prior to calculating a CT image into the raw data. Methods of model-based estimation and measurement with dedicated sensors are used successfully in commercially available dual-source systems.

Strictly speaking the method of model-based estimation (i) assumes that when scanned in sequential mode, the object does not change or only changes insignificantly during a spiral scanning along the feed direction (z-direction). With an increased z-coverage of the detector with simultaneously high values for the pitch during spiral scanning, this estimation of the scattered beam profile is however increasingly incorrect. On the other hand, with these methods disclosed for instance in the publication DE 10 2007 014 829 B3 (the entire contents of which are hereby incorporated herein by reference) for classifying the object tangents using scattered radiation, ambiguities appear in the determination of the scattering surface, which result in an inadequate estimation of the scattered beam profile appearing on the object.

The method of measuring the scattered radiation using dedicated sensors (ii) on the one hand requires additional hardware, which may determine a not insignificant part of the manufacturing costs of a dual-source device. On the other hand, with this method, the scattered beam profile is not measured directly at the z-position at which the correction is then implemented. Any variations in the z-profile of the scattered radiation are therefore not detected or only in a spatially sub sampled fashion. An increasing z-coverage of the detector results in an increasingly incorrect correlation of the measured scattered beam profile with the necessary correction of data.

The third method of alternate blanking of the respective primary radiation and direct measurements of the trans-verse scattering during the blanking phase (iii) nevertheless does not suffer from this potentially inadequate correlation of the data in the z-direction, but the data here can in turn not be scanned as precisely as may be required in the angular direction, which results in corresponding aliasing errors both in the scattered data and also in the primary data. In addition, the image noise increases by the blanking of the primary radiation. The dose efficiency is also less, since, in reality, the switch-on and off phases of the emitter cannot be arbitrarily short. A rapid blanking of the x-ray radiation not least makes high demands on the x-ray emitter and high voltage generator of a CT device.

SUMMARY

In at least one embodiment of the invention, an improved method and an improved computer system are disclosed for scattered beam correction during a CT examination of an object in a multi-source CT.

Advantageous developments of the invention form the subject matter of subordinate claims.

The inventors have identified that the profile of the transverse scattering intensities appearing in a dual source scan can be determined from the reconstructed image data within the scope of an iterative image construction and can be used iteratively to correct the raw data. An improved approximation therefore results with each iteration step for the scattered beam intensity used in the raw data correction, in which:

$$f_{k+1} = f_k - Q(A \cdot f_k + S(f_k) - t) - R(f_k)$$

applies.

Here $f_k$ is the image in iteration step k, A is the operator of the forward projection, Q stands for the back projection, e.g. according to a WFBP method (WFBP=Weighted Filtered Back Projection), t represents the raw data exposed to scattered radiation and R represents a suitable regularization term.

In accordance with an embodiment of the invention, this iterative method can be implemented with the subsequently described different variants of scattered beam estimation S(G).

Variant 1: calculation of the transverse scattering from the retracing of a beam from the detector element to the initial image.

Detector arrangements with collimators form the basis here, whereby the individual detector elements are collimated onto the focus of the opposing tube, e.g. a 2D scattered beam grid can be used for this. On account of these collimators, original beams are defined for each detector element, scattering centers are identified along these in the object or reconstructed image and if necessary classified with respect to their scattering properties. For each scattering center i, the scattering angle $\theta_i$ is therefore known for a specific tube position, similarly the irradiated intensity and energy distribution of the scattering beam, so that the respective differential scattering cross-section can be calculated therefrom. In a second step, each of these calculated scattering amplitudes is subjected to an individual attenuation, which results from the line integral via the object attenuation, based on the site of the scattering center up to the point of the respective detector element. The scattering distribution is therefore calculated first, in other words a scattering event per quantum. The consideration of a limited number of scattering centers, which may also depend on the value of the line integral, also simplifies matters further. In the simplest case, only scattering centers can be examined on the object surface.

Higher orders, in other words several scattering events per quantum, can be included by cascading the described procedure, they are however very demanding in terms of computing time.

Variant 2: Determining the scattering surface from the initially reconstructed image.

This variant 2 is based on the knowledge that the transverse scattering effective on the image mainly occurs near to the surface of the scattered object. The more accurately the object surface is therefore known, the more precisely the transverse scattering distribution of the object can be determined. Within the scope of the iterative reconstruction, the following subvariants are conceivable here:

Subvariant a: determining the scattered beam profile from table access. This method represents an extension of the model-based transverse scattering correction. The selection of a specific, tabular scattered beam distribution per projection takes place here by assigning three parameters, for instance the width of the air gap between the object and detector of the transverse scattering, the width of the air gap between the object and x-ray source which causes the transverse scattering, and the angle between the normals of the scattering surface relative to the incident beam. Further parameters would in principle also be conceivable, for instance the angle between the surface normal of the scattering surface and the scattered beam would in principle be considered. In accordance with the invention, the object edge of interest is however taken directly from the initial or the last available reconstructed image. In addition, depending on the reconstructed layer thickness, the z-variation of the transverse scattering can also be taken into consideration, since a different parameter set results for each reconstructed layer.

Subvariant b: model of surface scattering. To simplify variant 1, the scattering for each of the original beams to the detector elements can be determined from a function $f(\theta,\phi)$. Here $\theta$ is the angle between the original beam of a detector element relative to the surface normal of the emission point on the curved object surface. The angle $\phi$ is the angle between this surface normal and the connecting line to the x-ray source. The function $f(\theta,\phi)$ characterizes the transverse scattering process taking place. If the underlying process of the transverse scattering was a simple reflection for instance (entry angle=exit angle), the function $f(\theta,\phi)$ would be proportional to Dirac's delta function: $f(\theta,\phi)=c\cdot\delta(\theta-\phi)$.

The mutual interaction of x-ray quanta with object surfaces is however more complicated. The scattering processes of the x-ray quanta taking place on the object surface, consisting of photo effect and Compton scattering, can be detected for instance by an analytical model in the function $f(\theta,\phi)$. A second possibility is the simulation of the situation with Monte Carlo methods. A third possibility consists in the direct measurement of the function for different angles $\theta,\phi$ and their storage in a two-dimensional table. The function $f(\theta,\phi)$ can herewith be determined as a weighted sum of components $f_n(\theta,\phi)$, so that $$f(\vartheta,\varphi) = \sum_n a_n \cdot f_n(\vartheta,\varphi)$$

applies. Each component n herewith represents the scattering on a surface of a specific order: e.g. plane, spheres with different radii etc. During the iterative reconstruction, the respective weights $a_n$ can be determined from the local surroundings of this point for each point of the surface. In the simplest case $f(\theta,\phi)$ can also only be approximated by the scattering on a plane: $f(\theta,\phi) \approx f_1(\theta,\phi)$.

Variant 3: Calculating the transverse scattering using Monte Carlo methods.

The prediction of the transverse scattering can also take place by way of a Monte Carlo method, whereby the path of a plurality of photons, originating from the source, is simulated through an object and as far as the detector. Here the Monte Carlo method can directly use the 3D attenuation distribution of the object initially reconstructed without scattering correction as a scattering object. This enables a very precise prediction relating to the scattered beam distribution. The method calls for considerable effort, however, since on the one hand, a beam tracing through a pixelated object requires numerous computing operations and on the other hand only few scattered photons reach the detector, as a result of which very many primary photos have to be simulated. Additionally, a multi component break-down of the initially or finally reconstructed energy-dependent image data can also take place in a known fashion in order to determine a material distribution. To speed up and simplify matters, the following subvariants can be used:

Subvariant a: In order to simplify and speed up the simulation, the object can be replaced by an object from a homogenous material, e.g. water.

Subvariant b: The actual object can be replaced by a similar geometric object, e.g. an elliptical cylinder, or a combination of several geometric objects.

Subvariant c: Additionally, the object in subvariant b can be composed of few materials, e.g. water and bones.

Subvariant d: The photons can only be traced up to a given scattering order, preferably only up to the first scattering order.

Subvariant e: In order to speed up the simulation and to reduce the noise on account of the minimal number of photons striking the detector, all detector channels can be struck from each alternating point comprising empirical values by scattering photons in accordance with known effective cross-sections and probabilities.

With all embodiments of the methods, the scattering on the patient couch can also be treated separately as an additional factor. The transverse scattering of the patient couch can be determined in advance for each reclining position in the measurement field, e.g. by means of direct measurement. Although the attenuation of the patient couch is generally negligible, the transverse scattering on the under side and on the lateral edges of the couch can contribute significantly to the overall transverse scattering intensity. If the threshold value was selected in the image for instance such that only points on the surface of the patient and within the patient are examined as scattering centers, this procedure provides an improvement to the scattering radiation model.

An advantage of at least one embodiment of the method is that it manages without additional sensors or without additional demands on the emitter or generator of a CT device. Compared with mode-based methods, there is an advantage that the approximate characterization of the object surface from the sinogram data can be replaced by a small number of temporally older tangents compared with the current measurement by way of a more robust characterization of the object surface from a currently reconstructed CT image. Ambiguities can therefore be prevented and the prerequisite of an object which is approximately homogenous in the z-direction can be avoided. A further advantage is the more flexible modeling of the transverse scattering.

According to the afore-cited basic ideas, the inventors propose an embodiment of a method for scattered beam correction in a CT examination of an object, in particular a patient, in a multi-source CT, in particular a dual source CT, comprising:

Scanning the object by way of at least two emitter-detector systems which are arranged angularly offset in a plane, whereby each emitter emits a beam bundle onto the respectively opposite detector and a scattered radiation grid is used on each detector, and generating original projection data records, reconstructing the object using the original projection data records of at least one detector;

determining the scattered radiation generated by each emitter exclusively in the direction of the original beams of the at least one other emitter to its opposing detector, generating corrected projection data records by removing the calculated scattered radiation from the original projection data records, reconstructing the object with the corrected projection data records, examining at least one abort criterion and implementing a further iteration of the method when determining the scattered radiation or issuing the reconstruction result if the result of the examination of the at least one stop criterion produces the same.

In accordance with an embodiment of the invention, one or a combination of several of the subsequent criteria can be used as a stop criterion: maximum number of iterations, equating the image results to a predetermined value and/or equating the determined scattering results to a predetermined value.

In an alternative embodiment of the method, it is advantageously proposed here to consider the scattered radiation appearing on the surface of the object exclusively.

In order herewith to determine the scattered radiation on the surface of the object, the local curvature of the surface of the object, the angle of incidence of the incident beam and the at least one emergent angle of the at least one emerging scattered beam in the direction of the at least one other detector can be considered. A 3-dimensional table can also be used here, in which, from preliminary tests, the scattered radiation values are entered on the basis of angle of incidence, emergent angle and surface curvature of the scattering object. Furthermore, the surface curvature of the scattering object can be determined on the basis of previously reconstructed image data.

According to another alternative of an embodiment of the method, in the overall object on at least one part of the points of intersection of the original beams of the beam bundle generating the scattered radiation and the other beam paths of the at least one other beam bundle for the respective other beam path, the intensity of the original beams and the developing scattered radiation can be exclusively determined in the direction of the at least one other beam path and its intensity on the detector by taking the attenuation in the object into account.

In order to determine the scattered radiation on the observed points of intersection, the scattered radiation can herewith also be calculated directly by a function which takes the angle of incidence, the scattering angle and the scattering material determined from the last reconstruction data into account.

In a particularly simple embodiment, a uniform material distribution can be assumed in order to determine the intensity and/or energy of the original beam at the site of the appearance of the scattered radiation. Furthermore, in order to determine the intensity of the original beam at the site of the appearance of the scattered radiation, a predetermined material distribution similar to that of the body or a material distribution can also be assumed, which is taken at least approximately from one of the preceding, in particular the last, reconstruction of the object.

Alternatively to the direct formula-based calculation, this can also be determined by a Monte Carlo simulation in order to determine the scattered radiation at the examined points of intersection. A uniform material distribution, and more advantageously a predetermined material distribution similar to that of the body or even more advantageously a material distribution can also be assumed here in the object, which is taken at least approximately from a preceding, preferably the last, reconstruction of the object.

In order to avoid excessively long computing times, it is also favorable with the Monte Carlo simulation to trace the photons only up to a predetermined scattering arrangement, in particular up to the first scattering arrangement.

With embodiments of the afore-cited methods, the already known scattering distribution of a patient couch can also be added to the determined object-related scattering distribution.

If an embodiment of the method is executed within the scope of a CT examination whereby either by the use of different x-ray spectra and/or the use of energy-resolving detectors, the possibility of a material break-down which is known per se is established, then such a previously calculated material distribution can be taken into account in the CT representation in order to determine the scattering.

Aside from the embodiments of the method, an embodiment of the invention also includes a computer system of a multi- or dual-source CT system having a memory for computer programs, whereby the memory also contains a computer program which implements the following method steps during operation:

Scanning the object by controlling at least two emitter-detector systems which are arranged angularly offset in a plane, whereby each emitter emits a beam bundle onto the respectively opposing detector and a scattered radiation grid is used on each detector, and generating original projection data records, reconstruction of the object with the original projection data records of at least one detector, determining the scattered radiation generated by each emitter exclusively in the direction of the original beams of the at least one other emitter relative to its opposite detector, generating corrected projection data records by removing the calculated scattered radiation from the original projection data records, reconstructing the object with the corrected projection data records, examining at least one abort criterion and implementing a further iteration of the method when determining the scattered radiation or issuing the reconstruction result, if the result of the examination of the at least one abort criterion produces this.

A computer system also lies within the scope of an embodiment of the invention, which does not have to be directly connected to a CT system and is embodied for image processing with a memory for computer programs, whereby the memory also contains a computer program which implements the following method steps during operation:
- receiving detector data or projection data from a scanning of an object,
- reconstruction of the object with projection data records of at least one detector calculated from the detector data or originally received,
- determining the scattered radiation generated by each emitter exclusively in the direction of the original beams of the at least one other emitter relative to its opposing detector,
- generating corrected projection data records by removing the calculated scattered radiation from the original projection data records,
- reconstruction of the object with the corrected projection data records,
- examining at least one abort criterion and
- implementing a further iteration of the method when determining the scattered radiation or issuing the reconstruction result, if the result of the examination of the at least one abort criterion produces this.

With embodiments of such computer systems, the computer program can naturally also be configured in the memory such that during operation it executes the other afore-cited steps of embodiment of the method.

BRIEF DESCRIPTION OF THE DRAWINGS

The invention is described in more detail below on the basis of the example embodiments with the aid of the figures, whereby only the features needed to understand the invention are shown. The following reference characters are used: 1: CT system; 2: first x-ray tube; 3: first detector; 3.1: scattered radiation grid; 4: second x-ray tube; 5: second detector; 5.1: scattered radiation grid; 6: gantry housing; 7: contrast agent applicator; 8: patient couch; 9: system axis; 10: computer system; Ba: first beam bundle; Bb: second beam bundle; i: scattering center; K: orbital path of the gantry; N: surface normal; O: original beam; P: patient/object; $Prg_1$-$Prg_n$: computer program; S: scattered beam; S1: scanning of the object; S2: generation of original projection data records; S3: reconstruction of the object with the original projection data records; S4: determining the scattered radiation generated by each emitter, exclusively in the direction of the respective other detector; S5: generating corrected projection data records; S6: reconstruction of the object with the corrected projection data records; S7: examination of at least one abort criterion; S8: issuing, storing or further processing the reconstruction result; Z: beam generating scattering; $\theta_i$: scattering angle at scattering center i; $\phi$: angle of incidence $\theta$: scattering angle.

In which, in detail.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of trans-mission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
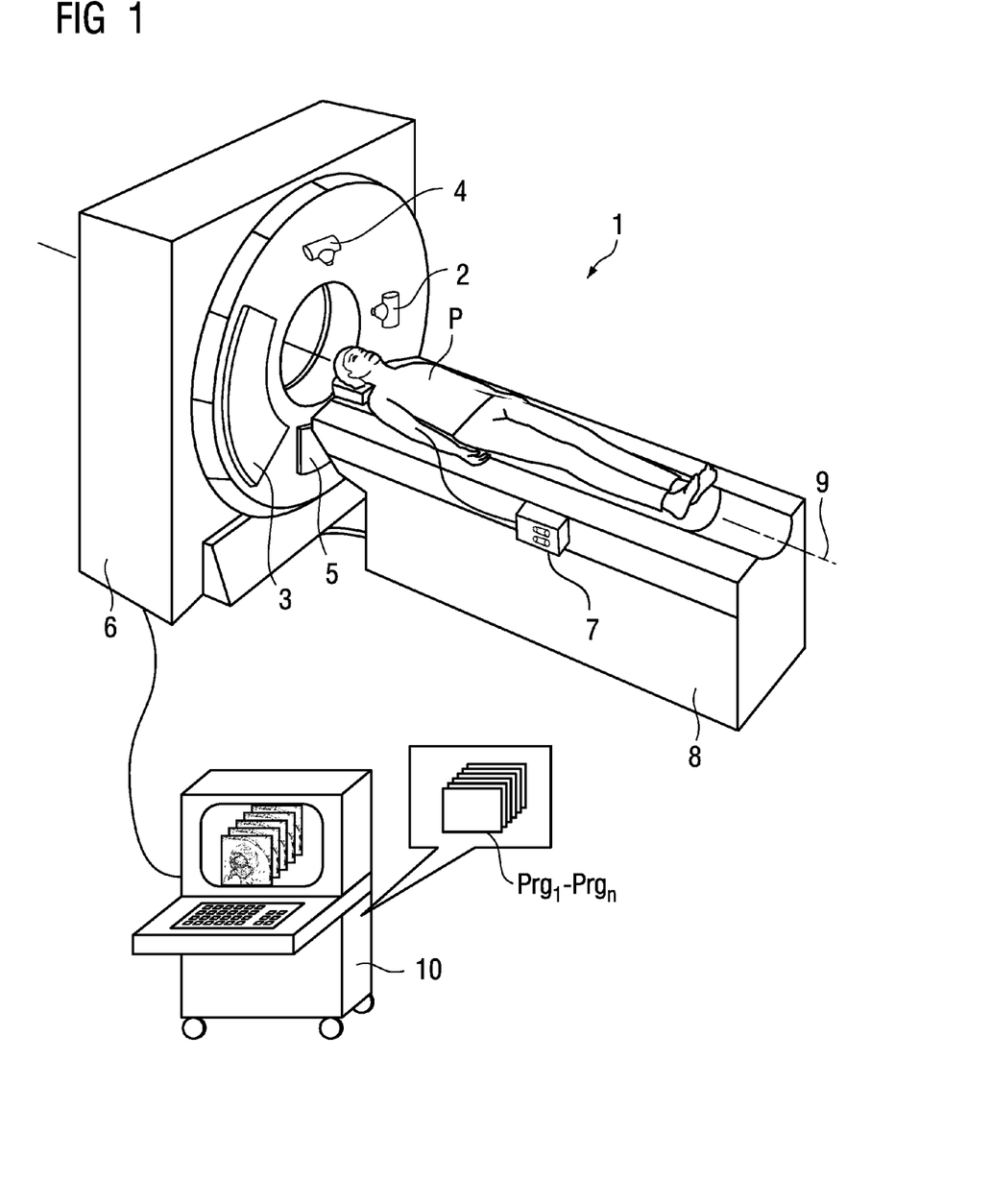
FIG. 1 shows a dual-source CT system.

FIG. 1 shows an example representation of a dual-source CT system (=CT system with two emitter-detector systems) 1 with a gantry housing 6, in which two emitter-detector systems which are arranged angularly offset are fastened to the gantry (not shown in more detail). The emitter-detector systems include a first x-ray tube 2 having a detector 3 assigned and opposite to the first x-ray tube on the one hand and of a second x-ray tube 3 having a facing detector 5 assigned to the second x-ray tube 4. Both emitter-detector systems spread a measurement field disposed in the central, round opening. The patient P can be moved through this measurement field along the system axis 9 with the aid of the patient couch 8. A spiral scan can herewith essentially also be executed as a sequential scan. In order to improve the image of blood vessels or other structures, a contrast agent can also be injected into the patient by way of the contrast agent applicator 7.

The control of the CT system 1 and the evaluation of the scanning of the patient P is executed by the computer system 10 connected thereto, whereby this comprises at least one memory, in which computer programs $Prg_1$-$Prg_n$ are stored. In accordance with the invention, programs are also contained and/or stored therein, which are embodied such that they implement the different embodiments of the inventive method during operation of the system.

Figure 2:
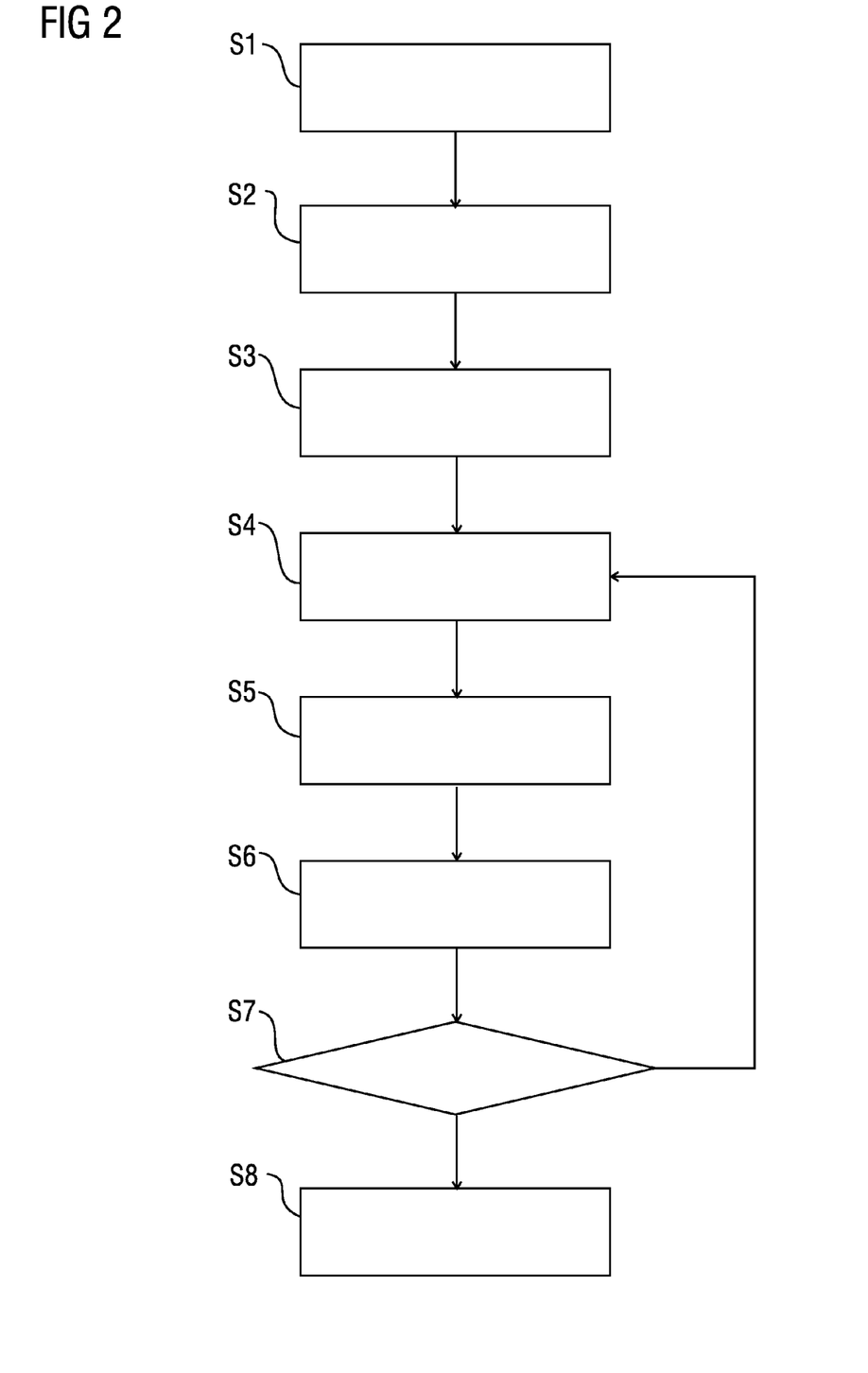
FIG. 2 shows a flow chart of an embodiment of the inventive method.

To represent an embodiment of the inventive method, a flow chart is shown in FIG. 2, which shows the basic method steps S1 to S8. In step S1, the object is scanned by way of at least two emitter-detector systems arranged angularly offset in a plane. An arrangement of the emitter-detector systems similar to FIG. 1 is herewith assumed, whereby each emitter emits an original beam bundle onto the respectively opposing detector. These original beam bundles simultaneously generate scattered radiation on the object, whereby however only those scattered beams are detected on a detector, which, on account of the scattered radiation grid used on each detector, run in the direction of the respective original beams.

In the second step S2, original projection data records are generated from the measured detector data.

With step S3, a CT representation of the scanned object is reconstructed with the original projection data records of at least one detector.

Subsequently in step S4, the determination of the scattered radiation generated by each emitter takes place exclusively in the direction of the original beams of the at least one other emitter relative to its opposing detector on the basis of the information available from the preceding reconstruction with respect to the embodiment of the object, in other words in particular its geometric data and/or material distributions.

In the next step S5, the influence of the previously calculated scattered radiation is removed from the original projection data records.

The reconstruction of the object with the scattered radiation-corrected projection data records now takes place in step S6.

Subsequently in step S7, at least one abort criterion is examined for the iteration and a decision is made as to whether a new determination of improved scattered data is to be continued further again with the changed CT image data in step S4 or whether the iteration is to be aborted.

In step S8, the issuing, storage or further processing of the reconstruction result finally takes place, in other words with respect to the CT image data freed from the influence of scattered radiation.

Figure 3:
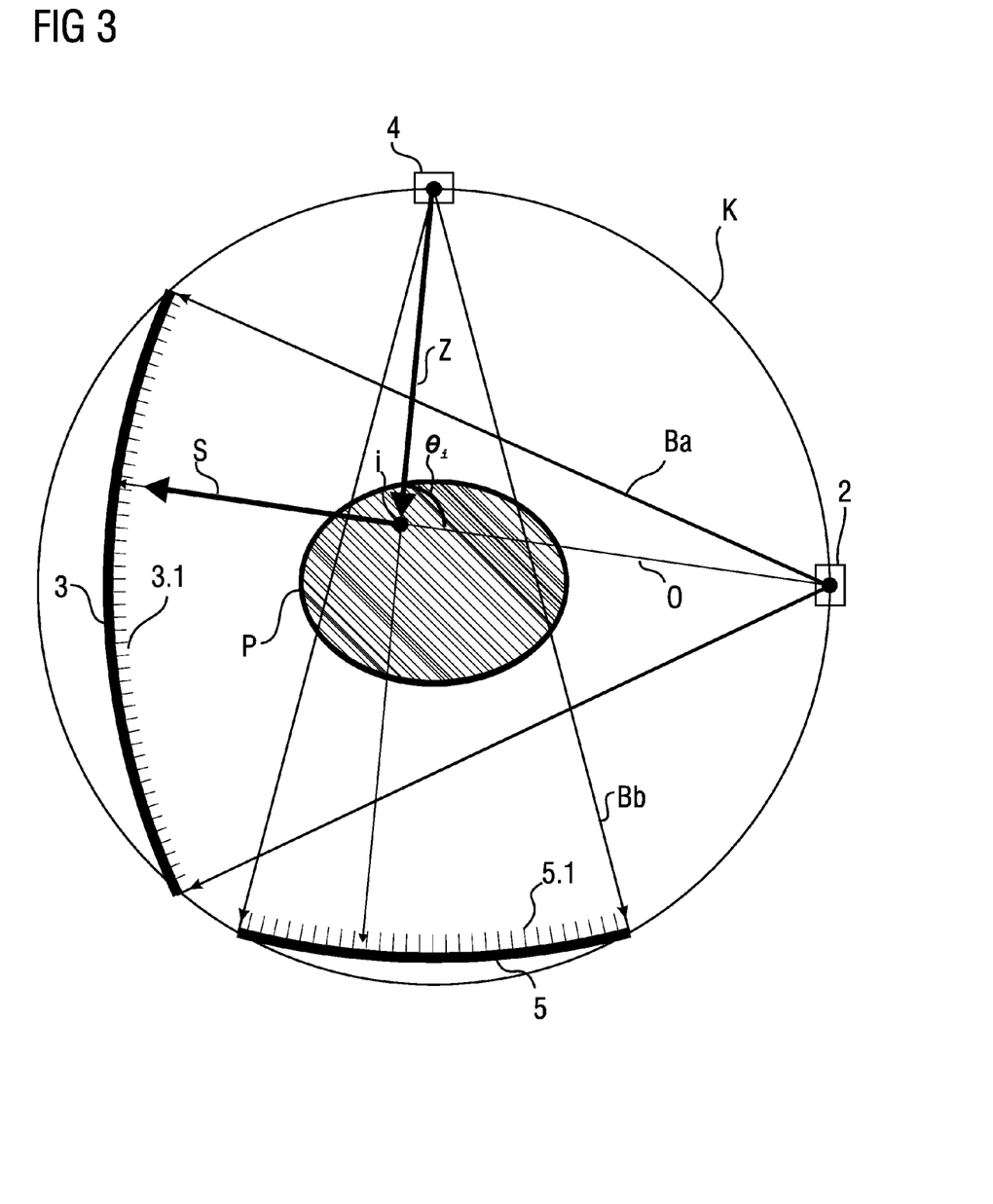
FIG. 3 shows a schematic representation of the calculation of a surface-related transverse scattering of an object and FIG. 4 shows a schematic representation of the calculation of a volume-related transverse scattering of an object.
Figure 4:
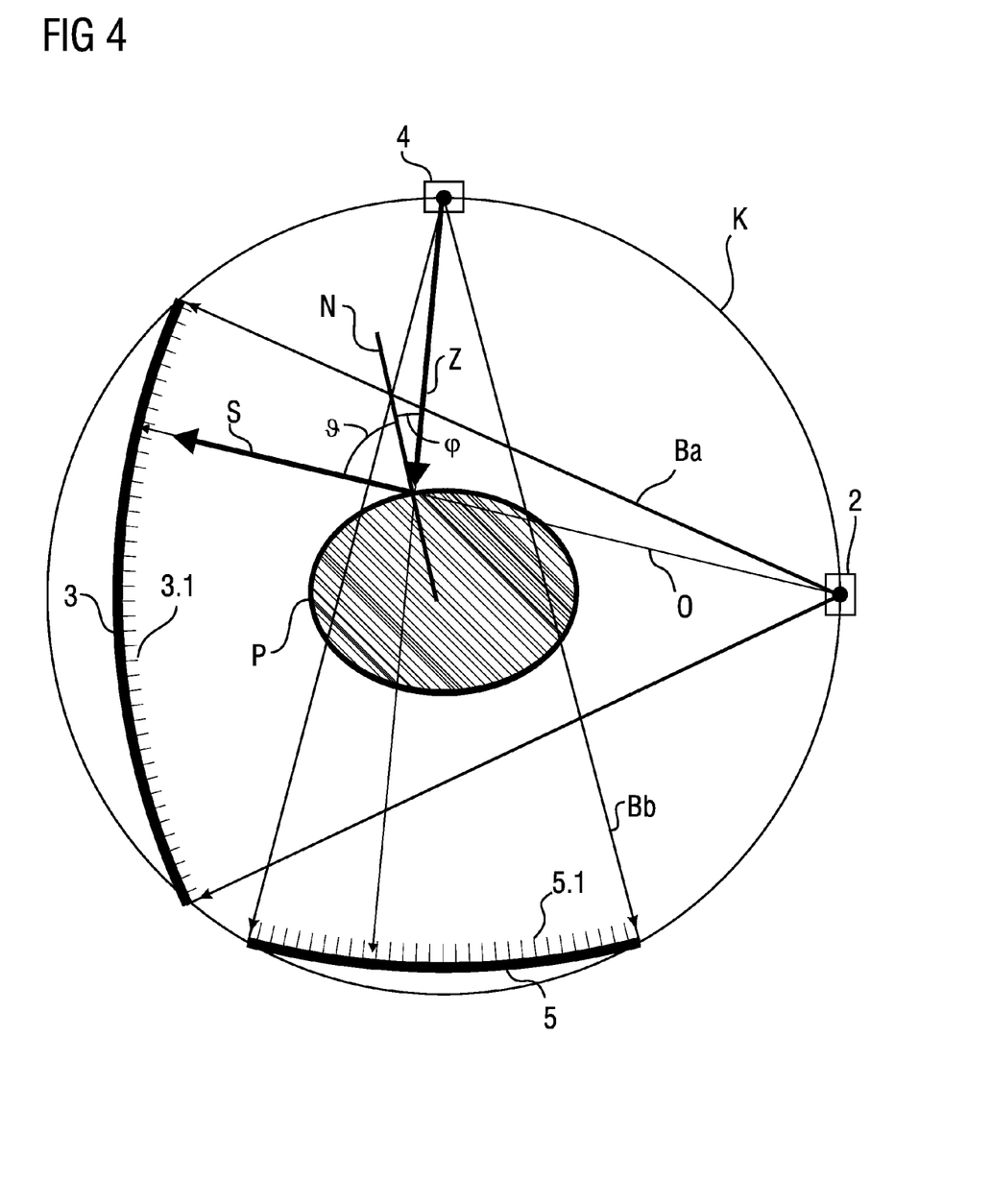

With respect to the determination of the scattered radiation which can be detected in the detector of the respective other emitter-detector system, a variant of determining by exclusively considering the surface or by considering the whole object is shown in FIGS. 3 and 4 in each instance.

FIG. 3 shows the orbital path K of the gantry, on which a first and a second emitter-detector system, which are arranged angularly offset, can be seen. The x-ray tube 2 and the opposite detector 3, between which the beam bundle Ba with the edge beams is shown, belong to the first emitter-detector system. The x-ray tube 4 and the opposite detector 5 between which the beam bundle Bb with its edge beams is shown, belong to the second emitter-detector system. Furthermore, a selected original beam O from the first tube 2 to the detector 3 is also apparent, upon which is superimposed by a scattered beam S, starting at the scattering center i, of a beam from the second tube 4. The scattering angle $\theta_i$ between the original beam 0 and the second beam z is likewise plotted.

FIG. 3 therefore shows the geometric ratios in the calculation of the transverse scattering from the tracing of an original beam from the detector element to the initial image. A plurality of scattering centers i lies along this original beam O.

The scattering angle $\theta_i$, at which the scattering radiation provides an unwanted contribution to the respective other emitter-detector system, is known for each of these scattering centers. The contributions of all points i, weighted with the attenuation through the object along the original beam can be calculated and totaled for the scattering contribution of the first order relative to this original beam. If this is implemented for all or at least a representative plurality of scattering centers, a good approximation therefore results for the intensity distribution of the scattering radiation actually occurring by taking the whole object into consideration.

An essentially similar situation is shown in FIG. 4, in which the determination of the scattering is exclusively shown on the surface of the object P. The structure of the emitter-detector systems is identical here to FIG. 3, whereby only scattering centers on the surface of the object P are examined and accordingly less scattering centers and their effect have to be calculated. The angle of incidence $\phi$ and scattering angle $\theta$ relative to the surface normal N are known here for all scattering centers on the surface, in accordance with the direction of the original beam and of the beam Z generating a transverse scattering. Accordingly, the scattering intensity generated there can also be calculated at the respective scattering center which is effective for a detector element and thus determined from a reconstructed CT image data record.

In summary, an embodiment of the invention therefore introduces a method and a computer system for scattered beam correction in a CT examination of an object in a multi-source CT, comprising:

generating original projection data records, reconstruction of the object with the original projection data records of at least one detector, determining the scattering radiation generated by each emitter exclusively in the direction of the original beams of the at least one other emitter relative to its opposing detector, generating corrected projection data records by removing the calculated scattering radiation from the original projection data records, reconstructing the object with the corrected projection data records, and implementing a further iteration of the method when determining the scattered radiation or issuing the reconstruction result if at least one predetermined abort criterion applies.

It is self-evident that the previously cited features of the invention cannot only be used in the respectively cited combination but also in other combinations or alone, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for scattered beam correction in a CT examination of an object in a CT system, comprising:
    scanning the object via at least two emitter-detector systems arranged angularly offset in a plane, each emitter of the at least two emitter-detector systems being adapted to emit a beam bundle toward a scattered beam grid of a respectively opposing detector of the at least two emitter-detector systems, and generating original projection data records based upon the scanning;
    reconstructing the object using the original projection data records obtained during the scan of the object from at least one detector of at least two emitter-detector systems;
    determining scattered radiation generated by each emitter of the at least two emitter-detector systems exclusively in a direction of original beams of the at least one other of the at least two emitters relative to a respectively opposing detector of the at least one other emitter, based on the reconstructed object, wherein scattered radiation produced on a surface of the object is exclusively taken into consideration;
    generating corrected projection data records by removing the determined scattered radiation from the original projection data records;
    reconstructing the object using the corrected projection data records;
    examining at least one abort criterion; and
    either implementing a further iteration of the determining of the scattered radiation, generating, reconstructing and examining, or issuing a result of the reconstruction, depending on a result of the examining of the at least one abort criterion.

2. The method as claimed in claim 1, wherein, in order to determine the scattered radiation on the surface of the object, a curvature of the surface of the object, an angle of incidence of an incidental beam and at least one emergent angle of at least one emerging scattered beam is taken into consideration in the direction of the at least one other detector.

3. The method as claimed in claim 2, wherein, in order to determine the scattered radiation, a 3-dimensional table is used, in which, from pretests, values of the scattered radiation are plotted based upon angle of incidence, emergent angle and surface curvature of the scattering object.

4. The method as claimed in claim 3, wherein the surface curvature of the scattering object is determined with the aid of previously reconstructed image data.

5. The method as claimed in claim 1, wherein an already known scattering distribution of a patient couch is added to the determined object-related scattering distribution.

6. The method as claimed in claim 1, wherein in order to determine the scattering, the material distribution is taken into consideration, by a material component breakdown taking place on the basis of energy-dependent attenuation values.

7. A non-transitory computer readable medium including program segments for, when executed on a computer device, causing the computer device to implement the method of claim 1.

8. The method of claim 1, wherein the CT system is a dual source CT system.

9. A method for scattered beam correction in a CT examination of an object in a CT system,
    scanning the object via at least two emitter-detector systems arranged angularly offset in a plane, each emitter of the at least two emitter-detector systems being adapted to emit a beam bundle toward a scattered beam grid of a respectively opposing detector of the at least two emitter-detector systems, and generating original projection data records based upon the scanning;

reconstructing the object using the original projection data records obtained during the scan of the object from at least one detector of at least two emitter-detector systems;

determining scattered radiation generated by each emitter of the at least two emitter-detector systems exclusively in a direction of original beams of the at least one other of the at least two emitters relative to a respectively opposing detector of the at least one other emitter;

generating corrected projection data records by removing the determined scattered radiation from the original projection data records;

reconstructing the object using the corrected projection data records;

examining at least one abort criterion; and either implementing a further iteration of the determining of the scattered radiation, generating, reconstructing and examining, or issuing a result of the reconstruction, depending on a result of the examining of the at least one abort criterion, wherein, in the overall object on at least one part of points of intersection of the original beams of the beam bundle generating the scattered radiation and the other beam paths of the at least one other beam bundle for the respective other beam path, intensity of the original beams and resulting scattered radiation is exclusively determined in a direction of the at least one other beam path by taking attenuation in the object into account.

10. The method as claimed in claim 9, wherein in order to determine the scattering radiation at the examined points of intersection, the scattering radiation is calculated directly by a function which takes an emergent angle, a scattering angle and scattering material specified from a last reconstruction material into consideration.

11. The method as claimed in claim 10, wherein in order to determine at least one of the intensity and energy of the original beam at a site of the appearance of the scattered radiation, a uniform material distribution is assumed.

12. The method as claimed in claim 10, wherein in order to determine the intensity of the original beam at a site of an appearance of the scattered radiation, a material distribution which is similar to that of the body is assumed.

13. The method as claimed in claim 10, wherein in order to determine the intensity of the original beam at a site of an appearance of the scattered radiation, a material distribution is assumed, which is taken at least approximately from a last reconstruction of the object.

14. The method as claimed in claim 9, wherein in order to determine the scattered radiation on observed points of intersection, the scattered radiation is determined by a Monte Carlo simulation.

15. The method as claimed in claim 14, wherein in order to calculate the Monte Carlo simulation, a uniform material distribution is assumed in the object.

16. The method as claimed in claim 15, wherein, with the Monte Carlo simulation, photons are only traced up to a first scattering order.

17. The method as claimed in claim 14, wherein in order to calculate the Monte Carlo simulation, a material distribution similar to that of the body is assumed in the object.

18. The method as claimed in claim 17, wherein, with the Monte Carlo simulation, photons are only traced up to a first scattering order.

19. The method as claimed in claim 14, wherein in order to calculate the Monte Carlo simulation, a material distribution is assumed, which is taken at least approximately from the last reconstruction of the object.

20. The method as claimed in claim 19, wherein, with the Monte Carlo simulation, photons are only traced up to a first scattering order.

21. The method as claimed in claim 14, wherein, with the Monte Carlo simulation, photons are only traced up to a first scattering order.

22. A computer system of a multi-or dual-source CT system, comprising:
   a processor; and
   a memory to store a computer program to implement at least the following during operation when run on the processor:
      scanning the object via at least two emitter-detector systems arranged angularly offset in a plane, each emitter of the at least two emitter-detector systems being adapted to emit a beam bundle toward a scattered beam grid of a respectively opposing detector of the at least two emitter-detector systems, and generating original projection data records based upon the scanning;
      reconstructing the object using the original projection data records obtained during the scan of the object from at least one detector of at least two emitter-detector systems;
      determining scattered radiation generated by each emitter of the at least two emitter-detector systems exclusively in a direction of original beams of the at least one other of the at least two emitters relative to a respectively opposing detector of the at least one other emitter, based on the reconstructed object, wherein scattered radiation produced on a surface of the object is exclusively taken into consideration;
      generating corrected projection data records by removing the determined scattered radiation from the original projection data records;
      reconstructing the object using the corrected projection data records;
      examining at least one abort criterion; and
      either implementing a further iteration of the determining of the scattered radiation, generating, reconstructing and examining, or issuing a result of the reconstruction, depending on a result of the examining of the at least one abort criterion.

23. A computer system embodied for image processing, comprising:
   a processor; and
   a memory to store a computer program to implement at least the following during operation when run on the processor:
      receiving detector data or original projection data from a scanning of an object via at least two emitter-detector systems,
      reconstructing the object with projection data records of at least one detector calculated from the detector data or original projection data,
      determining scattering radiation generated by each emitter, of the at least two emitter-detector systems, exclusively in a direction of original beams of at least one other emitter of the at least two emitter-detector systems relative to its opposite detector, based on the reconstructed object, wherein scattered radiation produced on a surface of the object is exclusively taken into consideration, generating corrected projection data records by removing the determined scattered radiation from the original projection data records, reconstructing the object with the corrected projection data records, examining at least one abort criterion, and either implementing a further iteration of the determining, generating, reconstructing and examining, or issuing a reconstruction result based upon a result of the examining.

24. A method for scattered beam correction in a CT examination of an object in a CT system, comprising:

reconstructing the object using original projection data records obtained during a scan of the object from at least one detector of at least two emitter-detector systems, the at least two emitter-detector systems being arranged angularly offset in a plane;

determining scattered radiation generated by each emitter of the at least two emitter-detector systems exclusively in a direction of original beams of the at least one other of the at least two emitters relative to a respectively opposing detector of the at least one other emitter, based on the reconstructed object, wherein scattered radiation produced on a surface of the object is exclusively taken into consideration;

generating corrected projection data records by removing the determined scattered radiation from the original projection data records;

reconstructing the object using the corrected projection data records;

examining at least one abort criterion; and either implementing a further iteration of the determining, generating, reconstructing and examining, of the scattered radiation or issuing a result of the reconstruction, depending on a result of the examining of the at least one abort criterion.

25. A non-transitory computer readable medium including program segments for, when executed on a computer device, causing the computer device to implement the method of claim 24.

26. The method of claim 24, wherein the CT system is a dual source CT system.

* * * * *